United States Patent [19]
Girndt et al.

[11] Patent Number: 5,600,069
[45] Date of Patent: Feb. 4, 1997

[54] ULTRASONIC TESTING APPARATUS AND METHOD FOR MULTIPLE DIAMETER OILFIELD TUBULARS

[75] Inventors: Richard J. Girndt, Spring; David E. Siverling, Houston, both of Tex.

[73] Assignee: ICO, Inc., Houston, Tex.

[21] Appl. No.: 429,517

[22] Filed: Apr. 26, 1995

[51] Int. Cl.$^6$ .................................................. G01N 29/04
[52] U.S. Cl. .............................................. 73/622; 73/628
[58] Field of Search ........................... 73/622, 625, 628, 73/637, 638, 640, 641; 976/DIG. 232; 376/252, 245; 364/507

[56] References Cited

U.S. PATENT DOCUMENTS

| | | | |
|---|---|---|---|
| 3,828,609 | 8/1974 | Furon et al. | 73/622 |
| 4,088,328 | 5/1978 | Roeder | 277/12 |
| 4,195,530 | 4/1980 | Ross et al. | 73/638 |
| 4,472,975 | 9/1984 | Beck et al. | 73/622 |
| 4,487,072 | 12/1984 | Livingston | 73/622 |
| 4,872,130 | 10/1989 | Pagano | 364/507 |
| 5,175,964 | 1/1993 | Girndt | 451/61 |
| 5,279,160 | 1/1994 | Koch | 73/622 |

FOREIGN PATENT DOCUMENTS 2027199A 2/1980 United Kingdom.

OTHER PUBLICATIONS

Article: A High-speed Ultrasonic Testing Machine for Tubes, By G. H. Kyte and K. R. Whittington, *The Radio and Electronic Engineer*, vol. 41, No. 5, May 1971.

Article: "Ultrasonic Transducer Array Configuration for Interlacing Scanning" By: K. H. Beck, *Materials Evaluation*, vol. 44, May 1988, pp. 771–778.

*Primary Examiner*—Christine K. Oda
*Attorney, Agent, or Firm*—Browning Bushman

[57] ABSTRACT

Ultrasonic testing apparatus 10 and method for ultrasonically scanning an oilfield tubular 42,56. The apparatus includes four ultrasonic arrays 12, 14, 16, 18 each containing a plurality of individual watertight ultrasonic transducers 20. Axially adjustable ultrasonic arrays 100, 121 include axially spaced sockets 102, 106, and 122, 124, 126, respectively, for controlling an axial movement thereof to preferably discrete positions associated with each selected range of diameters of oilfield tubulars to be tested. Within that range of diameters, the ultrasonic testing apparatus 10 reliably provides for a constant 100% coverage of the tubular to be tested. During scanning, the tubular 56 is moved axially and rotationally with respect to an ultrasonic testing apparatus 50 to provide a helical scan pattern along the length of the tubular 56.

12 Claims, 6 Drawing Sheets

ULTRASONIC TESTING APPARATUS AND METHOD FOR MULTIPLE DIAMETER OILFIELD TUBULARS

BACKGROUND OF THE INVENTION

1. Field of the Invention

The present invention relates generally to ultrasonic test head equipment and, more particularly, to equipment and methods for rapidly and reliably conducting ultrasonic testing including ultrasonic testing of multiple diameter oil field tubulars.

2. Description of the Background

The American Petroleum Institute (API) provides testing standards for oilfield tubulars. An oilfield tubular with a leak, a visually undetectable but internally corroded pocket, a hairline fracture, or other type of defect may create a hazardous condition and/or result in a costly and time consuming repair operation. Defects in oilfield tubulars have resulted in accidents causing injury, loss of expensive drilling strings, lengthy fishing jobs, and loss of recoverable hydrocarbons. Thus, it is cost effective and desirable to avoid a very expensive problem by the relatively inexpensive expedient of tubular testing.

Electromagnetic and/or ultrasonic testing of oilfield tubulars such as casing, drill pipe, and tubing is typically performed as a preventative measure after manufacture of the tubular. While electromagnetic testing of certain oilfield tubulars has been required for some time as per API standards, it is now recognized that ultrasonic testing is often a more critical test with respect to certain important factors such as wall thickness measurements and internal flaws. In fact, future API standards will require certain types of oil field tubulars to be ultrasonically tested.

Ultrasonic testing of oilfield tubulars is a relatively new service that has become available only in the last fifteen years or so. It has tended to be a rather time consuming procedure. However, if it is required by API standards that a substantial portion of the output of oilfield tubulars from the steel mills be ultrasonically tested, then large numbers of oilfield tubulars will need to be tested in a relatively short time period. Even with advances in ultrasonic test heads made in the last decade that provide more ultrasonic channels and a vastly increased helical advance per revolution of the tubular, ultrasonic testing has remained too slow to efficiently test the large numbers of oilfield tubulars that are produced by the steel mills. Thus, one of the most significant problems of prior art ultrasonic test heads is a slow testing speed.

General features of ultrasonic tubular testing equipment typically include drive means to translate/rotate a test head having one or more ultrasonic transducers with respect to the oilfield tubular to be tested. The test head and drive means typically produce a helical ultrasonic scanning pattern along the length of the oilfield tubular. For this purpose, the tubular may be held stationary while the test head moves over the exterior of the tubular. Alternatively, the ultrasonic test head may be stationary while the tubular is moved. To provide the helical scan pattern along the length of the tubular, it is necessary that the tubular rotate as well as move axially with respect to the ultrasonic transducer.

During the testing procedure, it is desirable to scan the tubulars slowly enough so as to reliably test the entire relevant surface area of the tubular. In other words, it is desirable to consistently provide a constant 100% scanning coverage of the tubular and avoid skipping over any portion of the tubular that might include a defect. On the other hand, it is also desirable to scan each tubular as rapidly as possible and without unnecessarily duplicating any testing.

While it is generally known to construct multiple ultrasonic linear arrays to increase the speed of inspection, the use of linear arrays also vastly complicates the problems of ultrasonic testing because of the large number of interrelated variables involved. Some of the factors and problems involved in utilizing ultrasonic linear arrays are discussed in the article "Ultrasonic Transducer Array Configuration for Interlaced Scanning" by K. H. Beck, *Materials Evaluation,* Vol. 44, May 1988, page 771–778. As stated therein, the denser interlacing arrangements used for this application with less than 180 degrees separation between the probe lines have resulted in fairly complex, inflexible, and inconvenient probe mounting and adjustments. Patents, such as U.S. Pat. Nos. 3,828,609 and 4,487,072, describe the general background and operation of ultrasonic testing equipment.

Ultrasonic linear array test heads provide an interlaced scanning configuration that is not efficient for each size diameter of pipe due to the numerous scanning factors that affect the skew angle or flaw pitch angle encountered as the surface of the tubular product passes by the test head at a fixed helix relative to the test head. Properly matching the optimal ultrasonic array configuration to the tubular diameter, the axial and rotational speeds of the tubular relative to the array, the diameter beam of each ultrasonic transducer, the orientation of the transducers, the distance from the transducers to the tubular, and the like, is difficult and time consuming.

Optimal array configuration means that the array provides a constant 100% scan of the tubular without unnecessarily duplicating the scan of all or part of the tubular. Given the numerous factors involved, prior art ultrasonic test heads employing linear transducer arrays frequently may not be efficiently adjusted to all tubular diameters and the related skew angles, and therefore sometimes scan less than 100% of the desired tubular to be tested. A defect may pass through the testing device undetected while other areas of the pipe are unnecessarily scanned multiple times.

Another related problem encountered during ultrasonic testing of tubulars is that of efficiently testing tubulars of varying diameters. U.S. Pat. No. 4,088,328 discusses a rapid changeover multi-diameter ultrasonic tube inspection system with rapid changeover features, and explains some of the difficulties involved in testing related tubulars used in nuclear power plants having varying diameters. As discussed in U.S. Pat. No. 4,088,328, the changeover time for converting some systems to handle different diameter tubulars may range from about four to eight hours. However, in the nuclear industry the need to test tubulars at high speeds is not nearly so great as it is in the oil industry.

Consequently, there remains a need to quickly and reliably provide adjustments to test heads that comprise multiple linear arrays of transducers to compensate for the varying skew angles created when tubulars are tested with different outside diameters or when increased helical advance speeds are used. Furthermore, there remains a need for an ultrasonic testing apparatus and method and that offers higher speed ultrasonic testing of oilfield tubulars that reliably provides constant 100% coverage thereof for a reasonable capitol investment. Those skilled in the art have long sought and will appreciate that the present invention provides solutions to these and other problems.

SUMMARY OF THE INVENTION

The ultrasonic test head apparatus of the present invention provides a reliable means for accurately ultrasonically testing oilfield tubulars at high speeds and includes efficient means for compensating for varying diameter tubulars. The ultrasonic test equipment includes a tubular support frame having a central axis and further comprises first and second linear arrays of transducers, each array including a plurality of ultrasonic transducers arranged along respective first and second array axes each substantially parallel to the central axis and laterally offset with respect to each other. A drive assembly operates to axially move an oilfield tubular with respect to the first and second linear arrays in a direction substantially parallel to the central axis. The drive assembly also rotates the oil field tubular with respect to the first and second linear arrays at a rate of rotation related to the axial movement. An axial adjustment assembly is used to adjust the axial position of the first linear array with respect to the second linear arrays as a function of the skew angle for the tubular being tested.

In operation, an oilfield tubular of a known diameter is placed onto the support frame for testing. The first linear array of ultrasonic transducers is moved axially as necessary with respect to the second linear array of ultrasonic transducers as a function of the skew angle of the oilfield tubular being tested. The oilfield tubular is moved both axially and rotationally with respect to the first and second linear arrays of ultrasonic transducers. At this time, the first and second linear arrays transmit and receive a plurality of acoustic signals towards and from the oilfield tubular to produce a typically helical scan pattern along the length of the oilfield tubular. Each transducer alternately transmits and receives its own signal in a pulse-echo manner and at a frequency that is fast enough to permit sampling in short time periods during which the oilfield tubular moves only a negligible distance. The axial positioning of the first and second linear arrays is adjusted to provide a desired skew angle that provides a constant 100% coverage of the oilfield tubular. If the diameter of the tubular is changed, then the axial positioning and/or the relative helical scan pattern may be adjusted accordingly to provide a desired skew angle. If the skew angle is determined to be within tolerances, it may be possible to scan a subsequently tested larger diameter tubular at a greater helical advance.

It is an object of the present invention to provide an improved ultrasonic assembly and method.

It is another object of the present invention to provide an ultrasonic testing assembly preferably for use at a steel mill that may reliably and quickly test oilfield tubulars having variable diameters.

It is yet another object of the present invention to provide an ultrasonic transducer array which utilizes axially adjustable, independent rods of equally spaced transducer elements to compensate for the varying flaw pitch angle encountered when multiple diameters of tubular products are inspected by means of the array, with a fixed helical relative advancement.

A feature of the present invention is a first ultrasonic transducer array that is movable axially with respect to a second ultrasonic array in a direction parallel to the central axis of a tubular support frame.

An advantage of the present invention is the elimination of extensive adjustments or modifications required to ultrasonically test oilfield tubulars having different diameters.

Another advantage of the present invention is the ability to reliably test a wide range of oilfield tubulars at high speeds with constant 100% coverage.

These and other objects, features, and advantages of the present invention will become apparent from the drawings, the descriptions given herein, and the appended claims.

While the present invention will be described in connection with presently preferred embodiments, it will be understood that it is not intended to limit the invention to those embodiments. On the contrary, it is intended to cover all alternatives, modifications, and equivalents included within the spirit of the invention or as defined in the appended claims.

DETAILED DESCRIPTION OF THE PREFERRED EMBODIMENTS

Figure 1:
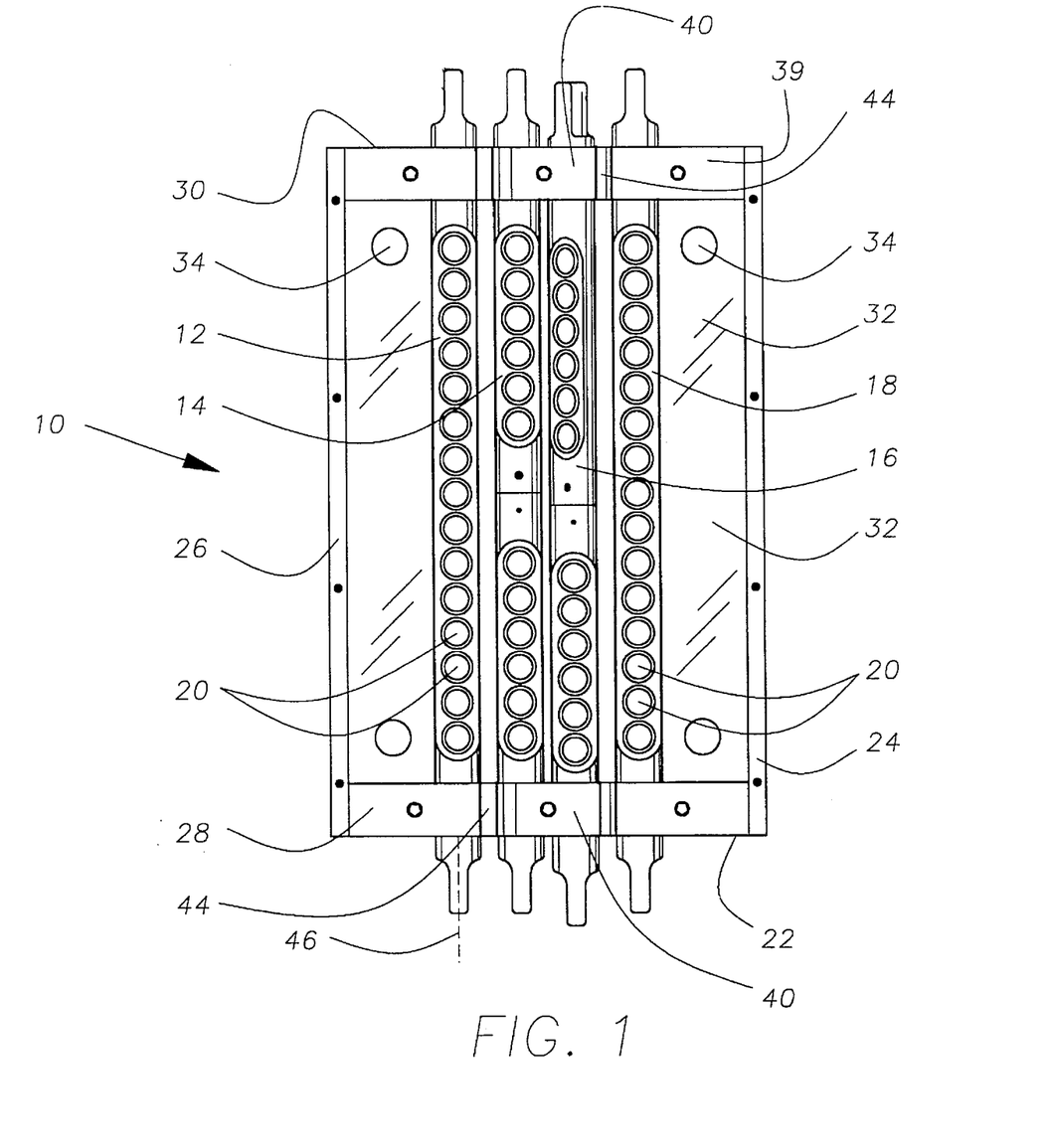
FIG. 1 is a top view of an ultrasonic tester in accord with the present invention.

Referring now to the drawings, and more particularly to FIG. 1, the general configuration of an ultrasonic test head assembly 10, in accord with the present invention, is illustrated. The present invention provides means for relatively high speed ultrasonic inspection with assured constant 100% coverage of tubulars regardless of such factors as varying diameters of the tubulars.

Ultrasonic test head assembly 10 includes four ultrasonic transducer rods or arrays, 12, 14, 16, and 18, comprised of multiple ultrasonic transducers such as watertight ultrasonic transducer elements 20. Ultrasonic transducer rods or arrays 12, 14, 16, and 18 are mounted within watertight test enclosure 22 that includes sides 24 and 26, end members 28 and 30, and bottom 32. In a presently preferred embodiment, rods 12 and 18 are identical. However, one the rods 12 and 18 is designed to be axially adjustable with respect to the other in a manner discussed hereinafter. As well, rods 14 and 16 are also preferably identical with either rod 14 or 16 being designed to be axially adjustable. Thus, in a presently preferred embodiment at least two of the four transducer rods 12, 14, 16, and 18 are axially adjustable.

Figure 1A:
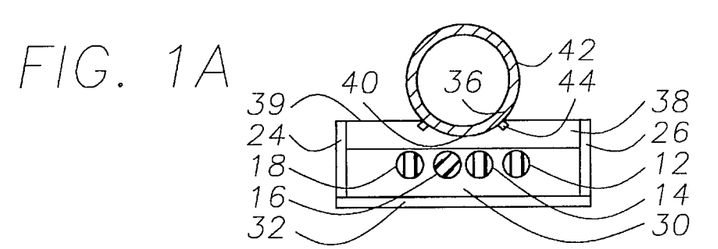
FIG. 1A is side elevational view, partially in section, of the ultrasonic tester of FIG. 1 positioned for testing an oilfield tubular.

Water or other acoustic couplant fluid may be introduced, maintained at a desired level, or removed from test enclosure 22 via ports 34. Thus, test enclosure 22 is a sealed structure, open at top 39 at least along slot or arched trough 40, and may be operated with a fluid medium to provide a suitable acoustic couplant between transducers 20 and oilfield tubular 36 as shown in FIG. 1A, The end sections of ultrasonic test head assembly 10, such as section 30 shown in FIG. 1A, include a replaceable bushing member 38 to provide suitably configured or arched trough 40 that substantially mates with the outer curvature 42 of tubular 36. Ceramic wear pins 44 may be used as desired to prolong the life of replaceable bushing member 38.

Transducers 20 are preferably parallel to axis 46 of each transducer rod and are also preferably parallel to axis 48 of the tubular to be tested. While the individual transducers are aligned in a linear manner, groups of transducers may be directed in different directions as desired to focus the acoustic signals with respect to the tubular dependent on the projected orientation of the flaw to be detected (see, for instance, FIG. 5).

The particular acoustic transducers used may vary between test heads with respect to the individual transducer diameter and/or effective transducer beam diameter, distance between transducer centers in the same transducer array, effective distance between transducer centers in different transducer arrays, number of transducers per array, distance between transducers and the tubular, and other such factors known to those skilled in the art. The transducer rods are typically rotationally oriented in different directions so as to maximize transmission and reception of acoustic signals as desired (see FIG. 6). The rate of axial and rotational (helical) advance may vary with testing configuration and the diameter of the tubular tested as discussed hereinafter. The helical advance may be adjustable as desired although it preferably remains constant during testing of a particular tubular.

Figure 2:
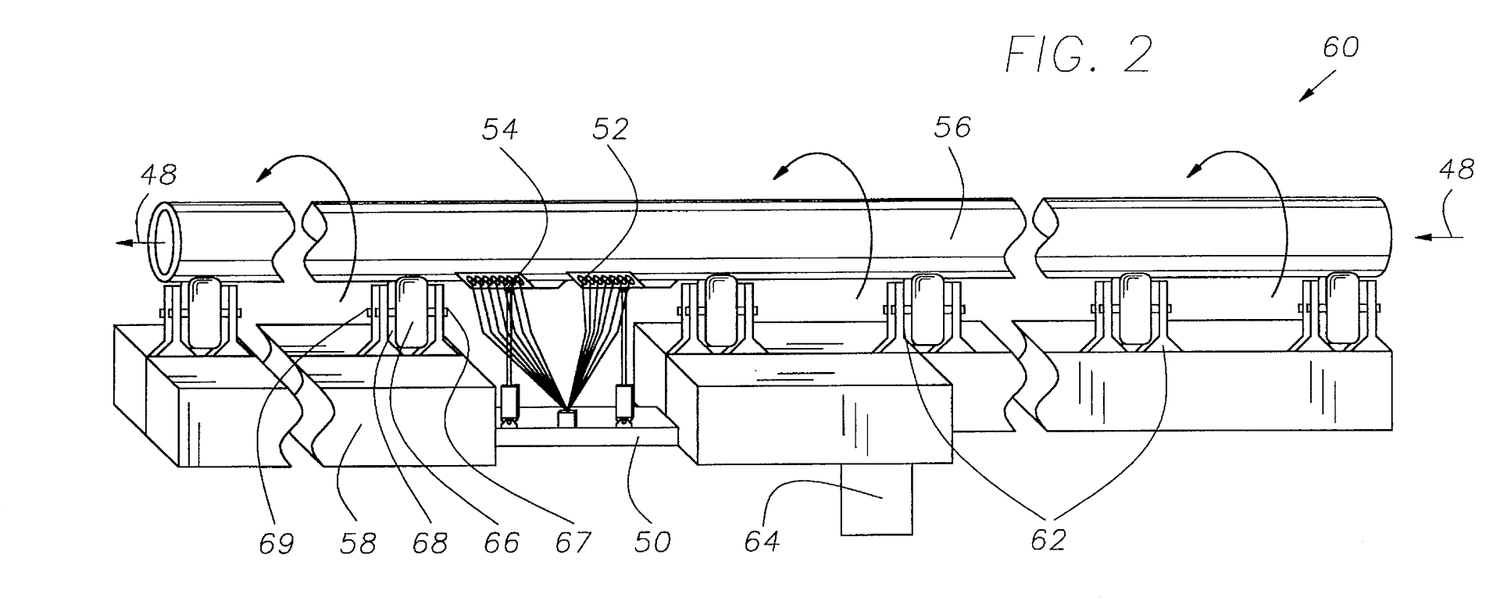
FIG. 2 is an perspective view of an ultrasonic transducer test head mounted for testing tubulars that are supported on a test frame.

In the present invention, the above factors are utilized in a computerized design process (see computer program listing at the end of the specification) to determine parameters of a system to provide constant 100% inspection coverage and to adapt the system to any particular diameter oilfield tubular and rate of helical advance thereof. Referring now to FIG. 2, test head assembly 50 includes multiple transducer arrays 52 and 54 for ultrasonically scanning oilfield tubular 56 as it is helically advanced (rotated and translated) along tubular support frame 58 at a fixed rate. Drive assembly 60 includes a plurality of rotator stations 62 that move oilfield tubular 56 axially and rotationally past test head assembly 50. Axial movement of tubular 56 is in a direction substantially parallel to tubular axis 48. For this purpose, each rotator station 62 has a pair of support wheels 66 and 68 disposed on opposite sides of tubular 56. Furthermore, rotator stations 62 are canted at a preferably selectable angle offset, from the perpendicular to tubular axis 48. By canted, it is meant that a line connecting between and/or perpendicular to respective axles 67 and 69, or axes of rotation of support wheels 66 and 68, is offset from a line perpendicular or orthogonal to axis 48 of tubular 56. Thus, as tubular 56 rotates, tubular 56 also necessarily moves axially in a direction parallel to tubular axis 48. Motor 64, or other means, may be used to rotate wheels 66 or other components for imparting a preferably constant rotation to tubular 56 during testing. Canted rotator stations 62 provide a constant axial motion per revolution as discussed hereinbefore. Other mechanisms to provide a preferably constant rotation and/or axial advance with respect to the tubulars to be tested may also be used.

The concepts of the present invention may be graphically represented in a two dimensional format to facilitate understanding of some of the factors involved in the three dimensional helical scan pattern of the pipe relative to a ultrasonic test head configuration. Analyzing the problem in this manner provides solutions that are easier to visualize for purposes of understanding the concepts involved. Thus, FIGS. 3A–3D graphically depict solutions provided by the present invention with respect to reliably providing high speed continuous 100% coverage for tubular testing as well as problems of scanning different diameter oilfield tubulars. It will be understood that while this graphical representation is used to more clearly convey the concepts involved, that the drawings are substantially simplified. For instance, the actual scanning pattern along the length of the tubular is a helical pattern rather than a purely straight line pattern.

Schematically indicated transducer arrays 72 and 74 form test head apparatus 73. Each transducer array 72 and 74 produces multiple transducer beams 76. Each transducer effective beam 76 is smaller in diameter than outer transducer casing 78 and transducer crystal 80. The oilfield tubular moves axially along or parallel to axis 82 as discussed hereinbefore with respect to FIG. 2.

Figure 3A:
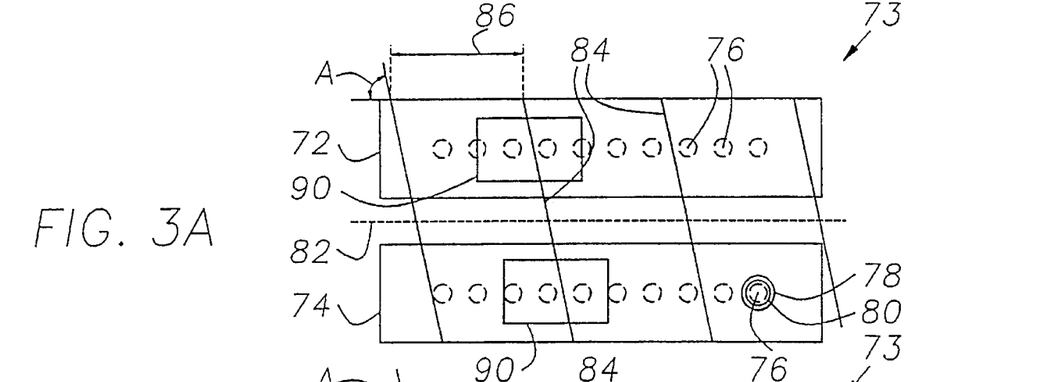
FIG. 3A is a simplified schematical representation of an ultrasonic array that provides less than a constant 100% ultrasonic scan coverage of a 4.5 inch O.D. tubular as the tubular is rotationally and axially advanced.

Referring now to FIG. 3A, as the tubular helically advances, a point on the tubular passes by transducer arrays 70 and 72 along lines 84. Lines 84 therefore represent, in a simplified manner, the path of a tubular defect passing by the transducer arrays. The scan paths of the ultrasonic transducers are understood to be parallel to lines 84 and include lines 84 if there is 100% constant coverage. The distance 86 between lines 84 preferably remains substantially constant for a particular diameter tubular and is the amount of axial advance of the tubular along axis 82 per rotation of the tubular. It may also be referred to as the helical advance per revolution of the tubular.

For this particular situation as depicted, respective calculations may include a 4.5 inch outer diameter tubular, with distance 86 being a helical advancement of three inches per rotation, and wherein a skew angle A is 78° with respect to axis 82 may be calculated. The skew angle A is effectively the angle of the helix of the scan path with respect to the axis of the ultrasonic array (that is typically parallel to the axis of the tubular) at the time the flaw passes by the respective transducer array. The skew angle is determined by numerous variables including the helical advance and the diameter of the tubular to be tested as per the program listing. Lines 84 are parallel to the scan paths along the tubular being tested.

As will be noted by looking within target region 90, it is possible for a potential defect positioned along lines 84 to pass through ultrasonic test apparatus 73 without being detected. Therefore, 100% constant coverage is not achieved for the schematically depicted test array configuration of FIG. 3A.

Figure 3B:
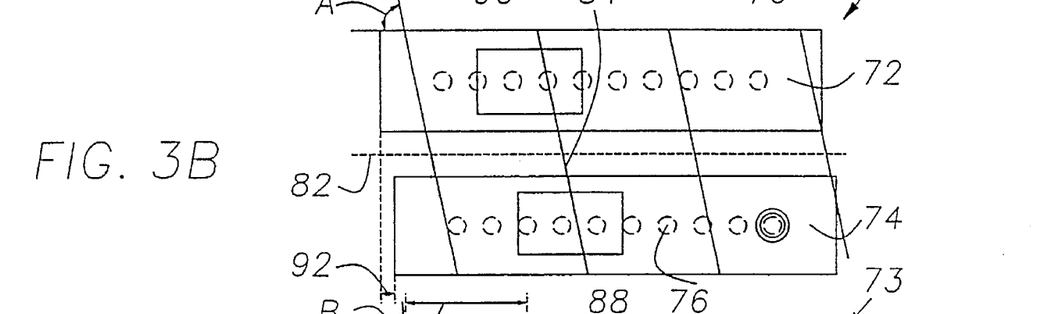
FIG. 3B is a simplified schematical representation of an ultrasonic array configuration that provides a constant 100% ultrasonic scan coverage of the 4.5 inch O.D. tubular of FIG. 3A.

Referring to FIG. 3B, and according to the method of this invention, transducer array 74 may be moved relatively, with respect to transducer array 72, by an axial distance 92 that is parallel to axis 82, in this case 0.27 inches, so as to improve efficiency and accuracy of the test head to provide constant 100% coverage of the tubular. The axial distance 92 is related to the skew angle and results in providing constant 100% coverage based on the skew angle for the configuration. The axial distance 92 may be determined by the computer program provided herein. After the relative shift is provided, it can be observed in FIG. 3B that while all other factors remain the same, the same defect traveling along lines 84 will now be detected by traveling through an ultrasonic beam. In fact, it will be noted that a defect travelling along any line drawn parallel to lines 84 having the same angle A or skew angle, will be detected by at least the outer edge of at least one of ultrasonic beams 76 or by a predetermined minimal portion of at least one of ultrasonic beams 76. Thus, the helical scan paths along the tubular now include all lines parallel to line 84 and there is 100% constant coverage of the tubular. It will be understood that sometimes it is desirable to have some overlap of the scanning paths and constant 100% coverage will be meant to imply at least a constant 100% coverage that may or may not include some scanning overlap.

Furthermore, as will be discussed subsequently, the computer program provided herein may be used to not only provide a particular adjustment for a particular diameter tubular, but also to calculate a range of pipe diameters, within which the axial distance need not be adjusted. Thus, according to the present invention, an axial adjustment need not be made for every change in pipe diameter, but only for changes in pipe diameter that are outside of a predetermined range of pipe diameters. The axial adjustment mechanism is required to make only a few, discrete, range-of-tubular-diameter type adjustments. Because adjustments need to be made only for a relatively few, discrete ranges of pipe diameters, it is possible to efficiently and inexpensively provide a much more accurate test head configuration.

Figure 3C:
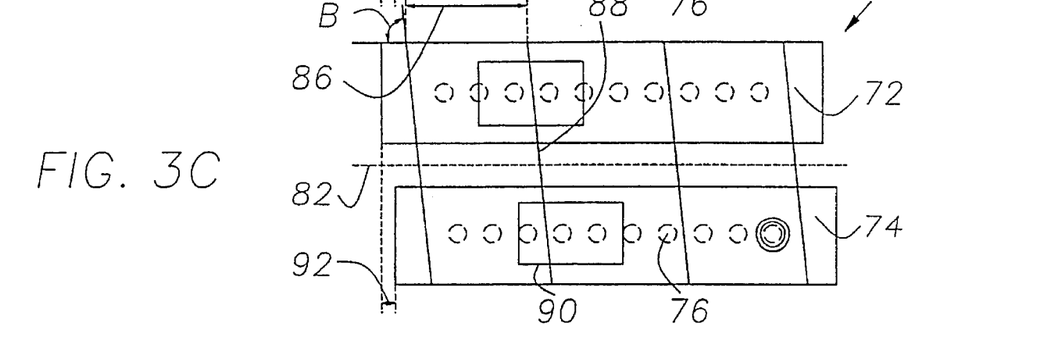
FIG. 3C is a simplified schematical representation of an ultrasonic array configuration that has the same transducer array offset as shown in FIG. 3B but now produces less than 100% ultrasonic scan coverage for a 9.625 inch O.D. tubular that is substituted for the 4.5 inch O.D. tubular of FIG. 3B.

FIG. 3C provides another example that shows the effect of axially translating a 9.625 inch outer diameter tubular by the same axial distance 86 per revolution (helical advance) as was made with the 4.5 inch tubular. As can be seen, a defect travelling along lines 88 past transducer arrays 72 and 74 will now be undetected due to the variation of skew angle B, now 84° with respect to tubular axis 82, caused by the increase in diameter of the tubular. Thus, the helical scan path of the transducers with respect to the axis of the pipe has a skew angle of 84° as it passes by the transducer arrays. However, the coverage is less than a 100% constant coverage of the pipe as noted by looking within target region 90.

Figure 3D:
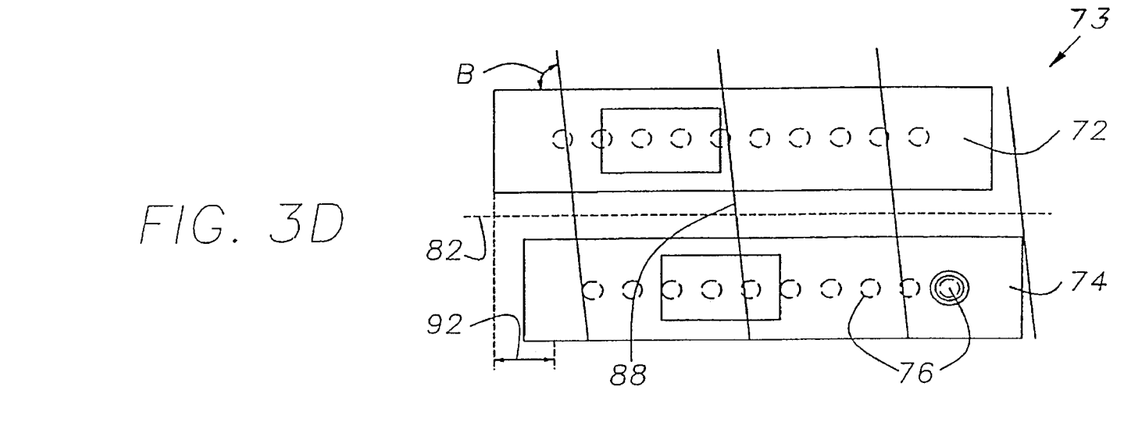
FIG. 3D is a simplified schematical representation of an ultrasonic array configuration that provides a constant 100% ultrasonic scan coverage of the 9.625 inch O.D. tubular of FIG. 3C.

FIG. 3D shows the effect of providing a relative axial shift distance 92 between arrays 82 and 84 equal to 0.711 inches to thereby provide 100% constant coverage of the tubular being tested. Now the scan path includes all lines parallel to lines 88 and that also includes lines 88.

Thus, for a given diameter of pipe or a given helical advance, using the present invention it is possible to calculate an axial shift distance 92 between similarly oriented rows of transducers to achieve a desired level of coverage, which may include some amount or percentage of overlap, for a given diameter or range of diameters of oilfield tubulars. While specific diameters, beam widths, distance between beams, etc. have been utilized herein as examples of operation, it will be readily understood by those skilled in the art that many other specific values for variables could have been used and that these were provided merely for convenience in understanding of the teachings of this specification. Furthermore, it will be appreciated by those skilled in the art that FIGS. 3A–3D are very simple graphical depictions of a much more complicated process.

Figure 4:
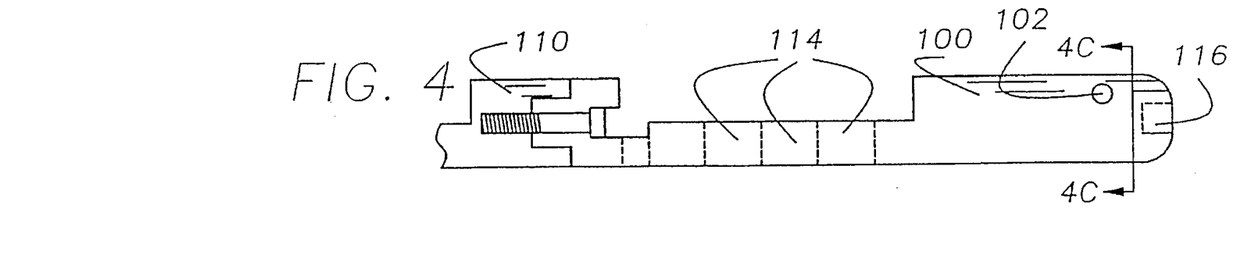
FIG. 4 is an elevational view of a first ultrasonic transducer array in accord with the present invention.
Figure 4A:
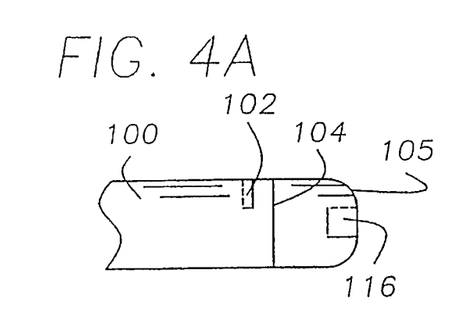
FIG. 4A is an enlarged view of the end portion of the transducer array of FIG. 4.
Figure 4B:
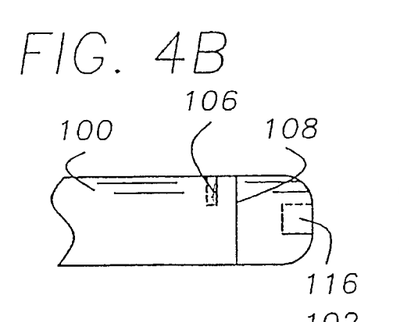
FIG. 4B is a view of the end portion of the transducer array of FIG. 4A showing a different setting corresponding to a range of pipe diameters.
Figure 4C:
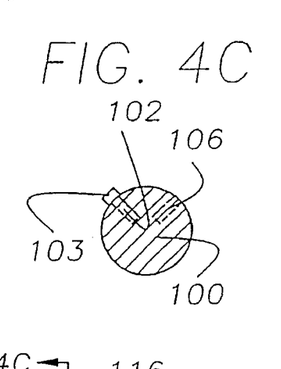
FIG. 4C is a view of the transducer array of FIG. 4 along the lines 4C—4C.
Figures 5, 5A, 5B, 5C, 5D:
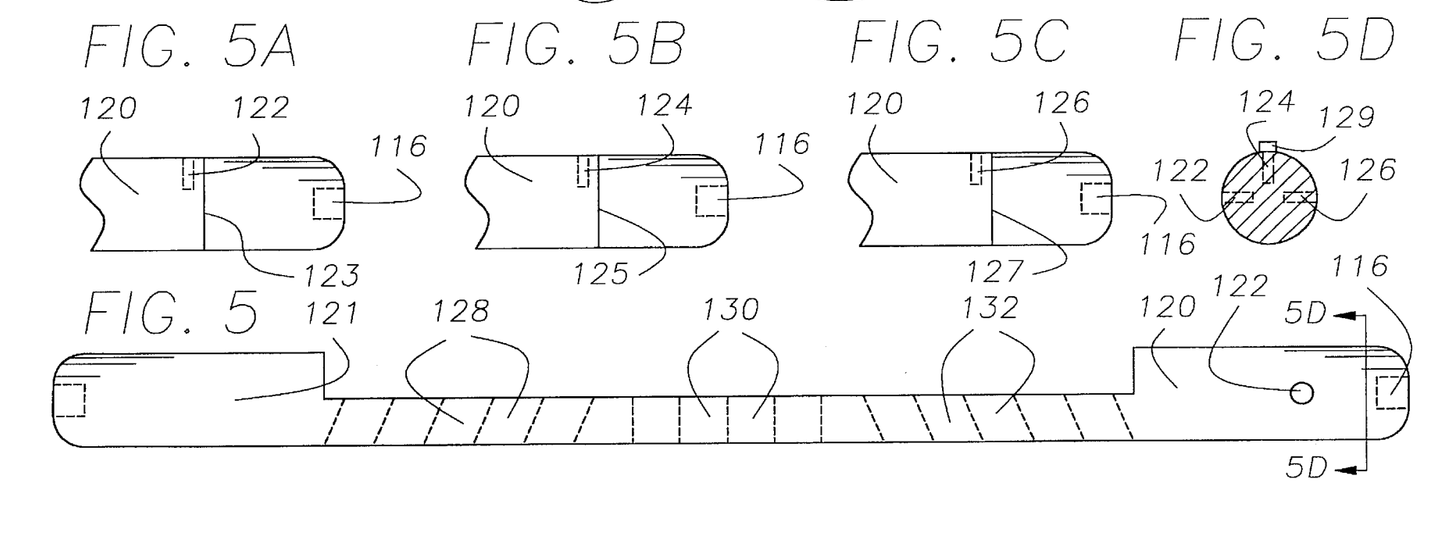
FIG. 5 is an elevational view of a second ultrasonic transducer array in accord with the present invention.
FIG. 5A is an enlarged view of an end portion of the transducer array of FIG. 5.
FIG. 5B is a view of the end portion of the transducer array of FIG. 5A showing a different setting corresponding to a range of pipe diameters.
FIG. 5C is a view of the end portion of the transducer array of FIG. 5A and FIG. 5B after further rotation.
FIG. 5D is a view of the transducer array of FIG. 5 along the lines 5D—5D.

FIGS. 4–5 disclose a presently preferred means of providing a desired amount of relative axial shift between respective transducer linear arrays shown schematically as arrays or rods 72 and 74 in FIG. 3A–3D. While a presently preferred means of providing the relative axial shift is disclosed, it will be clear that other mechanical implementations may be used to provide the axial shift.

End section 100 of linear transducer array 110, shown in FIG. 4, includes therein adjustment openings 102 and 106 that are axially spaced with respect to each other and from end 105. Openings 102 and 106 are also circumferentially spaced to allow for finer axial adjustment. If the openings were drilled in-line in the presently preferred embodiment, they would intersect each other. Scribe marks 104 and 108 are also provided to make the required axial adjustment more readily discernable. A pin 103 or other connector means is preferably provided for selecting and fixing a predetermined axial adjustment. End 105 may preferably be provided with a square socket 116, or other means, to allow rotation of the array or rod as necessary. FIG. 4 also illustrates a plurality of transducer mounting holes 114 in the end section 100 each for receiving a respective transducer therein.

Figure 6:
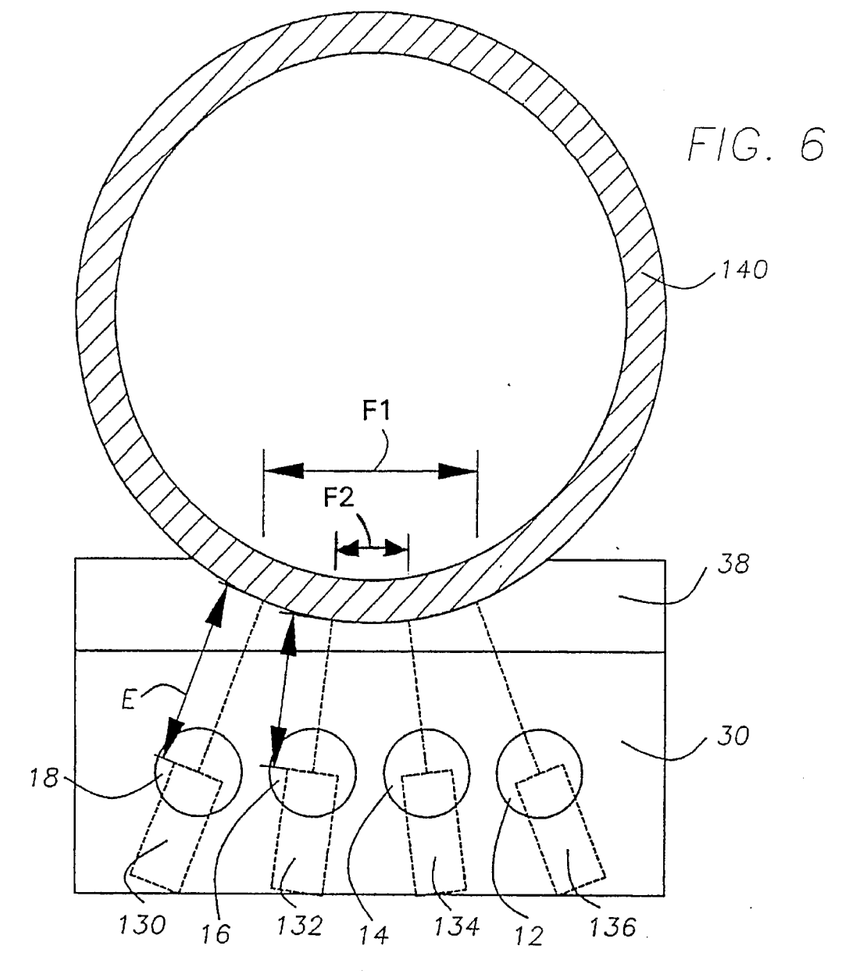
FIG. 6 is an elevational view, in cross-section, that shows a particular rotational alignment of transducer arrays with respect to an oilfield tubular.

In the presently preferred embodiment, end section 120 of adjustable linear transducer array 121, shown in FIG. 5, and which preferably corresponds to transducer array 12 of FIG. 6, is used in cooperation with an identical fixed linear transducer array such as transducer array 18 shown in FIG. 6. Adjustable transducer array 110, shown in FIG. 4, and which preferably corresponds to transducer array 14 in FIG. 6, is also used in cooperation with an identical fixed linear transducer array such as transducer array 16 shown in FIG. 6. However, the present invention is also clearly applicable for use with a test head having only two linear transducer arrays.

End section 120 provides three axially spaced adjustment openings 122, 124, and 126 that may be holes, slots, grooves, or other suitable adjustment means. Respective scribes 123, 125, and 127 may also be provided for visual ease and simplicity of operation. Adjustment openings 122, 124, and 126 are also circumferentially offset with respect to each other, as well as axially spaced with respect to each other. FIG. 5D illustrates pin 129 in opening 124.

Figure 7:
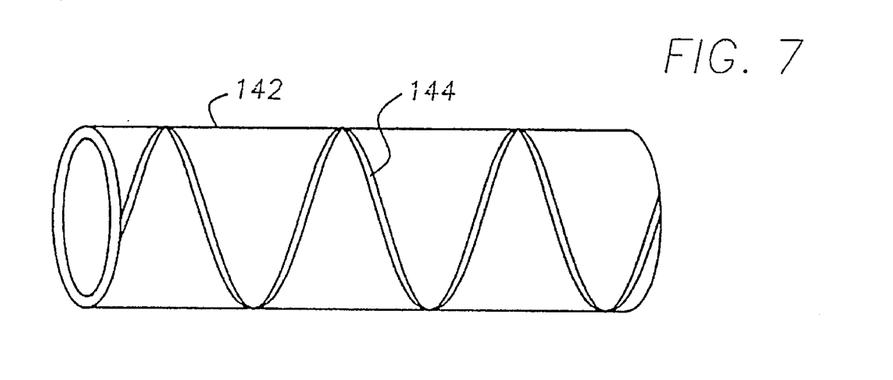
FIG. 7 is an elevational view that schematically shows a helical scanning pattern of an ultrasonic transducer along the length of an oilfield tubular.

Axially aligned groups of transducers 128, 130, and 132 are aligned to detect the same defect or flaw but may be pointed toward the leading/trailing side or right/left side of a particular flaw. The transducers may also be rotationally offset with respect to each other to maximize the signal response (see FIG. 6). As shown very generally in FIG. 6, the transducer arrays may be rotationally oriented using, for instance, one alignment transducer 130, 132, 134, 136 from each array that may be provided for alignment purposes. The signal from the alignment transducer may be monitored, in a preferred embodiment, for a maximum or desired amplitude signal that would typically indicate the desired rotational positioning. In determining the coverage provided by the test head, as well as for making skew angle calculations, various distances must be determined such as distance E from each of the transducers (which distance may vary between different transducer arrays), through the acoustic couplant, to the surface of the tubular 140. Distances, such as distances F1 and F2, between the locations where the ultrasonic beams encounter surface of tubular 140 need to be calculated to determine the effective distances between the arrays for the scanning signal applied to tubular. FIG. 7 provides a schematical representation of that displays a helical scanning path 144 of an ultrasonic transducer along the length of tubular 142.

In operation, a particular axial adjustment of arrays of linear transducers for a given range of tubular diameters is predetermined and written on a chart or indicated by the scribe lines discussed hereinbefore. Thus, an operator can quickly and conveniently adjust operation of ultrasonic test apparatus for different ranges of tubular diameters. As will be noted, the preferred number of ranges is conveniently limited so that adjustments are required as seldom as possible. Transducer array 121 has three positions while transducer array 110 has two positions because the distances F1 and F2 are different, as shown in FIG. 6, so that transducer array 121 requires a wider range adjustment capability. As discussed hereinbefore, transducer array 121 corresponds to transducer array 12 as shown in FIG. 6 while transducer array 110 corresponds to transducer array 14 of FIG. 6. It is contemplated that less than ten positions could easily cover the entire range of tubular diameters that might be scanned. In the presently preferred embodiment, only two transducer arrays are moveable while the remaining transducer arrays are axially fixed. Each of the two movable transducer arrays is adjustable with respect to one of the fixed transducer arrays. The two transducer arrays or rods are moved axially as necessary to provide constant 100% inspection coverage in response to changing the diameter size of the tubular to be tested.

Although the presently preferred embodiment conveniently requires only a few discrete adjustments, other axial adjustment mechanisms could be used. For instance, a mechanism could be provided to make an axial adjustment prior to testing each different size diameter oilfield tubular to be tested, rather than the preferred embodiment discrete pin-socket mechanism that is adjusted only once for a range of diameter sizes.

The computer program disclosed herein provides a means for calculating and graphically displaying an offset for a particular diameter tubular, or range of tubular diameters, for similarly oriented rows of transducer to achieve the desired coverage. The variables necessary include pipe diameter, number of transducers used, effective transducer beam diameter, distance between transducer centers within a given row, effective lateral distance between transducer centers between rows, the axial advance of the tubular (helix), the distance between the transducers and the tubular, and the like. Once these variables are set, the proper axial offset distance 92 can be determined that is related to the skew angle, and the adjustable row of transducers placed at a position to achieve the desired coverage. As well, a range of pipe diameters can be determined which will satisfy the requirement for a desired coverage that may typically include some overlap. In some cases, for instance, it may be possible depending on the skew angle to provide a larger diameter tubular and test it more rapidly than a previously tested smaller diameter tubular because the skew angle is within the necessary range for constant 100% coverage even with a greater axial advance per revolution of the tubular. The various testing situations and consequences of different variables may be determined or analyzed, preferably prior to operation, using the program.

The testing speed may also be limited by the frequency of operation of the transducers which frequency should be fast enough so that measurement is not affected by the movement of the tubular. It will also be understood that while scanning is made over the length of the tubular, some regions of the tubular, such as interconnections or end regions may not be tested.

The foregoing disclosure and description of the invention is illustrative and explanatory thereof, and it will appreciated by those skilled in the art, that various changes in the size, shape and materials as well as in the details of the illustrated construction or combinations of features of the various ultrasonic test elements may be made without departing from the spirit of the invention.

What is claimed is:

1. Ultrasonic testing apparatus for ultrasonically testing oilfield tubulars, said test apparatus including a tubular support frame having a central axis, said ultrasonic testing apparatus further comprising:

first and second linear arrays of transducers for unltrasonically testing said oilfield tubulars, each of said first and second linear array including a plurality of ultrasonic transducers arranged along respective first and second array axes each substantially parallel to said central axis and laterally offset with respect to each other;

a drive assembly operable for axially moving an oilfield tubular with respect to said first and second linear arrays in a direction substantially parallel to said central axis, and for rotating said oilfield tubular with respect to said first and second linear arrays at a rate of rotation related to said axial movement, the drive assembly including a plurality of canted rotator stations mounted along said tubular support frame, with each canted rotator station including two wheels adjacent each other for supporting said oilfield tubular therebetween and being canted with respect to said central axis of said tubular frame support; and an axial adjustment assembly for adjusting an axial position of said first linear array with respect to said second linear array in a direction substantially parallel to said central axis.

2. The ultrasonic testing apparatus of claim 1, wherein each of the first and second arrays include a plurality of transducers spaced substantially equidistantly from each other.

3. The ultrasonic testing apparatus of claim 1, further comprising:

a third linear array of transducers; and a second axial adjustment assembly for adjusting the axial position of said third linear array of transducers.

4. The ultrasonic testing apparatus of claim 1, further comprising:

means for determining said axial position of said first linear array with respect to said second linear for a skew angle of an ultrasonic scanning pattern produced when moving said oil field tubular with respect to said first and second linear arrays.

5. A method for ultrasonic testing oilfield tubulars, comprising the following steps:

providing at least two transducer rods for selective axial positioning along respective parallel transducer rod axes;

providing a plurality of ultrasonic transducers on each of said at least two transducer rods for ultrasonically testing said oilfield tubulars;

providing a tank containing acoustic couplant;

positioning said at least two transducer rods to produce ultrasonic signals within said tank;

positioning a first oilfield tubular with respect to said tank so as to be in acoustic communication with said acoustic couplant;

providing movement controls for moving said oilfield tubular with respect to said at least two transducer rods operable to result in a helical ultrasonic scan pattern along said first oilfield tubular; and controlling said axial positioning of said at least two transducer rods and said moving of said first oilfield tubular to adjust said helical ultrasonic scan pattern for constant 100% coverage along said first oilfield tubular.

6. The method of claim 5, wherein said step of controlling further comprises:

providing a plurality of discrete selectable axial positions for one of said transducer rods, at least one of said axial positions being correlated to a skew angle for said first oilfield tubular.

7. The method of claim 5, further comprising:

positioning a second oil field tubular having a different diameter from said first oilfield tubular with respect to said tank so as to be in communication with said acoustic couplant; and selectively controlling said axial positioning of said at least two rods to adjust said helical ultrasonic scan pattern for constant 100% coverage along said second oilfield tubular.

8. The method of claim 5, further comprising:

positioning a second oilfield tubular having a different diameter from said first oilfield tubular with respect to said tank so as to be in communication with said acoustic couplant; and selectively controlling said movement controls to adjust said helical ultrasonic scan pattern for constant 100% coverage along said second oilfield tubular.

9. The method of claim 5, further comprising:

positioning a second oilfield tubular having a different diameter from said first oilfield tubular with respect to said tank so as to be in communication with said acoustic couplant; and determining when said step of controlling should be repeated to provide for constant 100% coverage along said second oilfield tubular.

10. The method of claim 5, further comprising:

rotating each of said at least two transducer rods with respect to said first oilfield tubular while monitoring an alignment signal.

11. The method of claim 5, further comprising:

determining a distance between each of said plurality of transducers and an external surface of said first oilfield tubular.

12. The method of claim 5, further comprising:

determining a skew angle for said helical ultrasonic scan pattern.

* * * * *